United States Patent
Morgan et al.

(10) Patent No.: US 6,944,506 B1
(45) Date of Patent: Sep. 13, 2005

(54) STYLET FEATURE FOR RESISTING PERFORATION OF AN IMPLANTABLE LEAD

(75) Inventors: Kevin L. Morgan, Simi Valley, CA (US); Joseph J. Florio, La Canada, CA (US)

(73) Assignee: Pacesetter, Inc., Sylmar, CA (US)

( * ) Notice: Subject to any disclaimer, the term of this patent is extended or adjusted under 35 U.S.C. 154(b) by 427 days.

(21) Appl. No.: 10/180,789

(22) Filed: Jun. 25, 2002

(51) Int. Cl.[7] .................................................. A61N 1/05
(52) U.S. Cl. ....................................... 607/122; 600/585
(58) Field of Search ........................ 600/585; 607/122, 607/123, 125; 606/108; 604/164.01, 164.13, 604/170.02

(56) References Cited

U.S. PATENT DOCUMENTS

| | | | |
|---|---|---|---|
| 4,791,939 A | * | 12/1988 | Maillard ..................... 606/129 |
| 4,796,642 A | * | 1/1989 | Harris ......................... 600/585 |
| 5,261,419 A | * | 11/1993 | Osypka ....................... 607/122 |
| 5,505,686 A | * | 4/1996 | Willis et al. ................. 600/104 |
| 5,722,425 A | | 3/1998 | Boström ...................... 128/772 |
| 5,728,148 A | | 3/1998 | Boström et al. ............. 607/116 |
| 5,752,915 A | | 5/1998 | Neubauer et al. ........... 600/373 |
| 5,755,766 A | * | 5/1998 | Chastain et al. ............. 607/122 |
| 5,803,928 A | | 9/1998 | Tockman et al. ............ 607/122 |
| 5,807,339 A | | 9/1998 | Boström et al. ............. 604/164 |
| 5,935,160 A | | 8/1999 | Auricchio et al. ........... 607/122 |
| 6,192,280 B1 | * | 2/2001 | Sommer et al. ............. 607/122 |
| 6,389,320 B1 | * | 5/2002 | Pianca ......................... 607/122 |
| 6,456,890 B2 | * | 9/2002 | Pianca et al. ................ 607/122 |

FOREIGN PATENT DOCUMENTS

| | | | | |
|---|---|---|---|---|
| WO | WO98/32375 | 7/1998 | ............. | A61B 5/04 |
| WO | WO99/55412 | 11/1999 | ............. | A61N 1/05 |
| WO | WO99/64100 | 12/1999 | ........... | A61M 25/01 |

* cited by examiner

*Primary Examiner*—Kennedy Schaetzle

(57) ABSTRACT

A stylet unit for implanting a removable lead system for a cardiac stimulation device includes an elongated main body having an enlarged feature at the distal end of the main body with a rounded blunt tip end, a width greater than the width of the distal end of the main body, and a length greater than the width. A finger grip is provided at a proximal extremity of the elongated main body for manipulating the stylet unit. Lead system includes an elongated tubular lead body containing an elongated coil conductor with a plurality of coil windings defining a passageway extending the length of the coil conductor and having inner surfaces facing toward the passageway. The enlarged feature of the stylet is sufficiently long to assure that it advances along the passageway in slidable engagement with the inner surfaces of the coil conductor but without thrusting between adjoining coils.

8 Claims, 4 Drawing Sheets

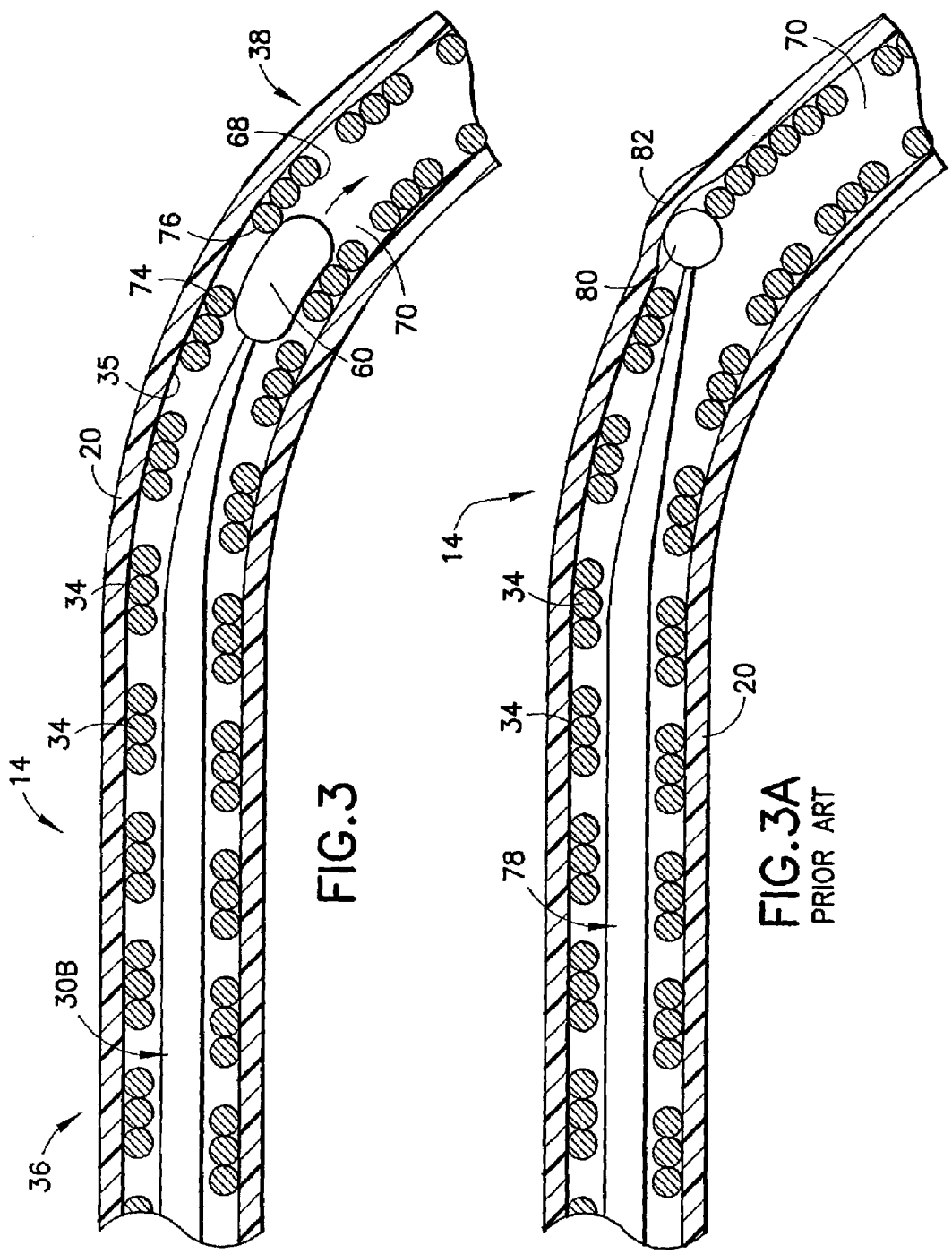

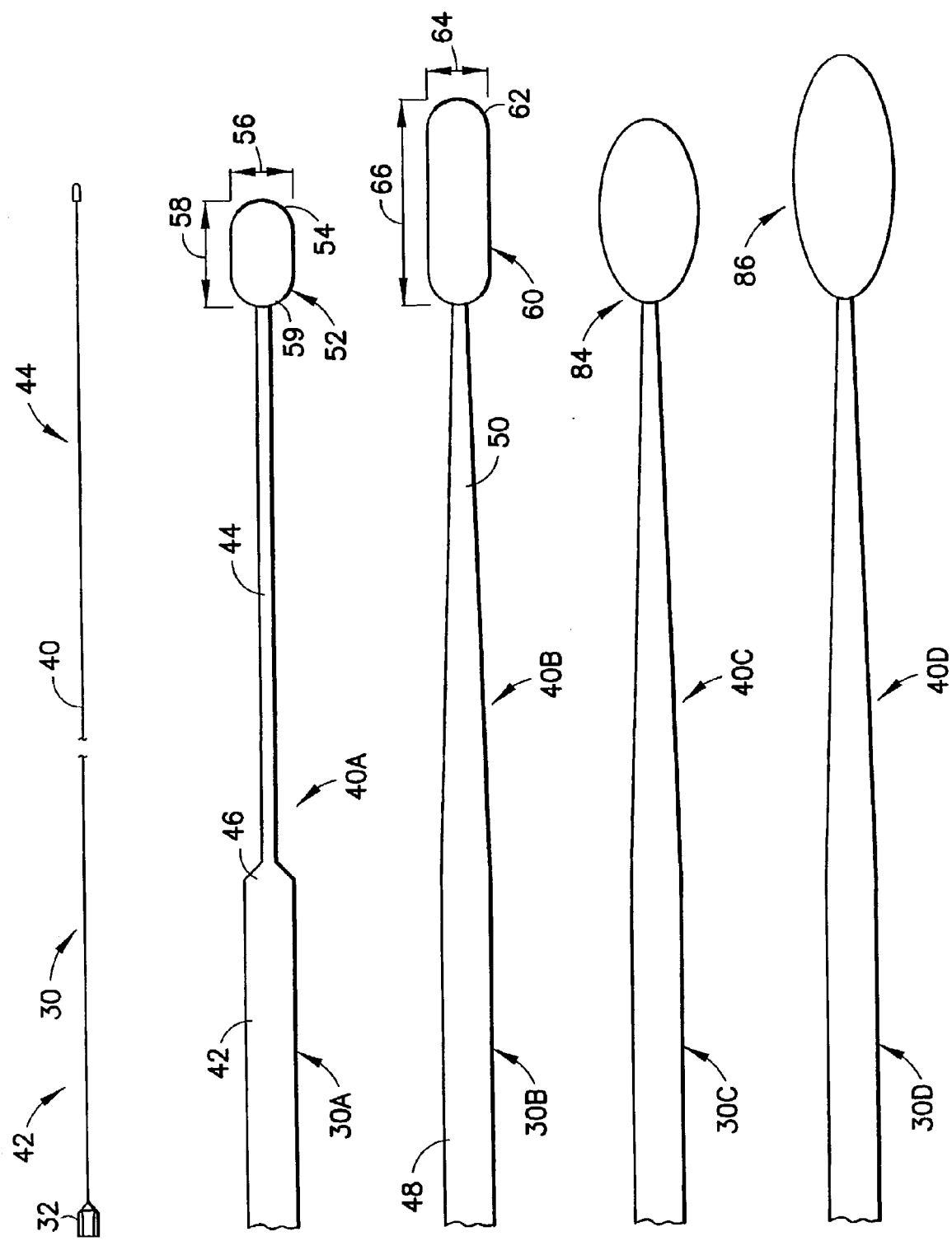

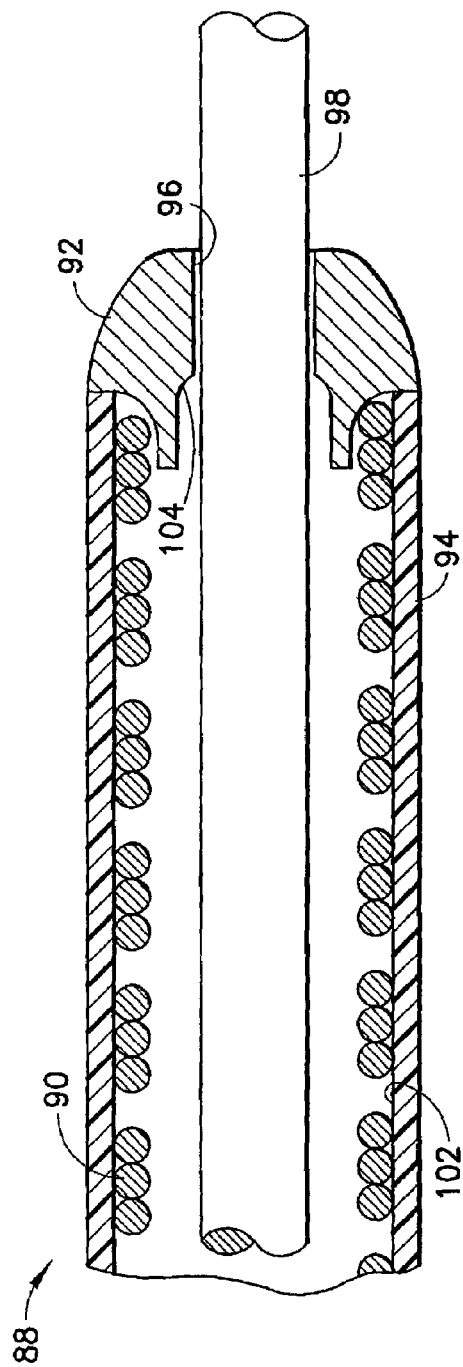
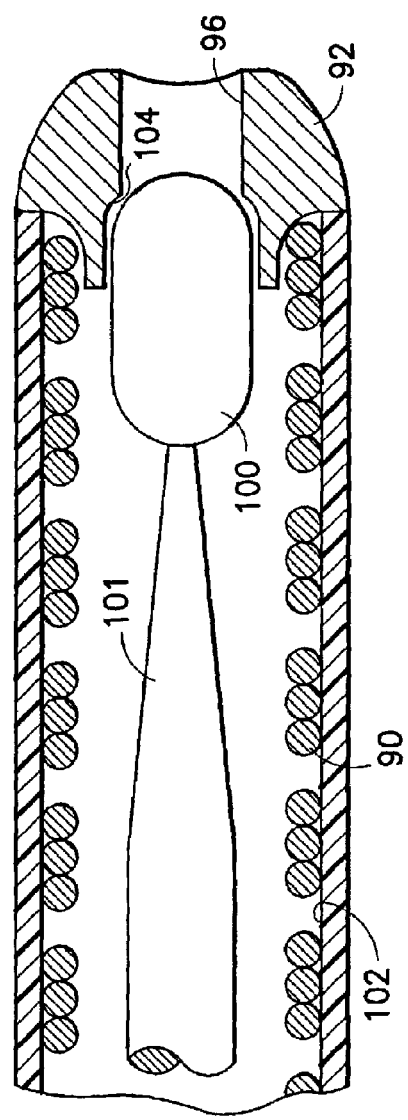

STYLET FEATURE FOR RESISTING PERFORATION OF AN IMPLANTABLE LEAD

FIELD OF THE INVENTION

The present invention relates to implantable leads for use with a cardiac stimulation device and, more particularly, to stylets which are used to facilitate the implantation of the lead into the body.

BACKGROUND OF THE INVENTION

Surgeons have implanted leads into the coronary sinus of the heart of a patient by using one of two methods to drive and position the lead. One method is to utilize a stylet to push the lead tip through the venous system when the stylet is fully inserted into the lead. The other method is to slide the lead over a guidewire. The lead has openings at each end through which the guidewire passes. The guidewire is positioned into the coronary sinus and the lead is then moved into position by sliding over the guidewire. Each method has its benefits. The problem is that, previously, it was necessary for the surgeon to choose which method to use prior to surgery.

Also, cardiac pacing and/or defibrillation leads are constructed generally using any of the following materials: silicone rubber, polyurethane, coil windings, cables with or without ETFE coating, and PTFE tubing. The lead is generally designed so a stylet can pass through the coil winding or PTFE tubing. The surgeon can then drive the lead into the desired location inside the heart using the stylet.

However, there are risks that are inherent to the procedure just mentioned. The lead must follow the venous system of the body and can experience very tight and tortuous bends. These bends can create a strain on the lead and require a greater force to drive the lead. The stylet then has the risk of passing in between the coil windings of the lead or piercing the PTFE and perforating the lead. This perforation is dangerous to the patient. Tearing of the veins or cardiac tamponade is a distinct possibility.

Typical of the known prior art are U.S. Pat. Nos. 5,807,339 and 5,728,148 to Boström et al. and U.S. Pat. No. 5,722,425 to Boström, each of which discloses a stylet unit which can be introduced into a hollow, flexible, component such as an electrode cable for a heart stimulator, to stiffen the component and to bend a distal end section, is in the form of a double stylet combination with a flexible tubular stylet shell and an internal stylet, movably arranged inside the shell, with a pre-curved distal end section, whose radius of curvature is on a first side of the stylet.

U.S. Pat. No. 5,935,160 to Auricchio et al. and U.S. Pat. No. 5,803,928 to Tockman et al. both disclose implantable lead systems which can be implanted by either a stylet or a guidewire.

It was in light of the foregoing that the present invention was conceived and has now been reduced to practice.

SUMMARY OF THE INVENTION

A stylet unit for implanting a removable lead system for a cardiac stimulation device includes an elongated main body having an enlarged distal feature at the distal end of the main body with a rounded blunt tip end, a width greater than the width of the distal end of the main body, and a length greater than the width. A finger grip is provided at a proximal extremity of the elongated main body for manipulating the stylet unit. The lead system includes an elongated tubular lead body containing an elongated coil conductor with a plurality of coil windings defining a passageway extending the length of the coil conductor and having inner surfaces facing toward the passageway. The enlarged distal feature of the stylet is sufficiently long to assure that it advances along the passageway in slidable engagement with the inner surfaces of the coil conductor but without thrusting between adjoining coils.

This invention combines the stylet and guidewire implantation method into one lead and also resists the possibility of stylet perforating the lead. At the time of implanting the lead, the surgeon may choose either method for placing the lead into the coronary sinus. This is made possible by reason of the design of the distal tip of the lead and the distal tip of the stylet.

The distal tip of the lead is designed so a guidewire is able to pass through it. This allows the surgeon to position the lead using the guidewire into the coronary sinus and into the left coronary veins. If the surgeon finds that the guidewire method is unsatisfactory and desires to use a stylet, he does not need to remove the lead. A specialized stylet can be used. This stylet is designed so the distal tip of the stylet stops at the distal tip of the lead. The lead is then positioned in the coronary sinus by way of the stylet.

According to the invention, an enlarged, elongated feature is incorporated at the distal end of the stylet. This feature is designed in such a manner that the force exerted by the surgeon is distributed over a larger surface area at the tip of the stylet. This reduces the pressure at any given point at the distal tip of the stylet and therefore reduces the risk of the stylet perforating the lead. The tapering of the stylet wire at the distal end further enhances this feature. The taper softens the resistance of the stylet to follow the bends in the venous system.

This combination of a larger surface area at the distal tip and tapering the wire to soften the bending resistance will lead to a greater reduction of stylet perforation through the lead. Furthermore, the larger surface area will more easily cross the gaps in the coil windings and resist piercing through them. The larger surface area will also resist distorting the PTFE tubing as the stylet passes through the tubing and will therefore resist piercing through it.

A primary feature, then, of the present invention is the provision of a unique stylet used to facilitate the implantation into the body of a lead for a cardiac stimulation device.

Another feature of the present invention is the provision of such a unique stylet which can resist perforating the lead into which it is inserted.

Yet another feature of the present invention is the provision of such a unique stylet which offers a surgeon, while in the midst of the surgical procedure, with the ability to choose whether to proceed with the use of a stylet in one instance or with the use of a guidewire in another instance.

Still a further feature of the present invention is the provision of such a stylet including an elongated main body extending between proximal and distal ends, having a width greater at the proximal end than at the distal end, and including an enlarged distal feature at the distal end of the main body having a rounded blunt tip end, a width greater than the width of the distal end of the main body, and a length greater than the width.

Yet a further feature of the present invention is the provision of such a stylet wherein, in one embodiment, the main body is tapered between the proximal end and the distal end; wherein, in another embodiment, the main body includes a proximal region of substantially constant width, a distal region of substantially constant width smaller than that of the proximal region, and an integral transition zone interconnecting the proximal region and the distal region; wherein, in still another embodiment, the enlarged distal feature is coaxial with the main body and has a substantially uniform width; wherein, in yet another embodiment, the enlarged distal feature has opposed sides substantially parallel with the axis of the main body and semicircular proximal and distal ends which are tangential, respectively, with the opposed sides thereof; and wherein, in still another embodiment, the enlarged distal feature is generally elliptical in shape having a major axis substantially coaxial with the main body.

Other and further features, advantages, and benefits of the invention will become apparent in the following description taken in conjunction with the following drawings. It is to be understood that the foregoing general description and the following detailed description are exemplary and explanatory but are not to be restrictive of the invention. The accompanying drawings which are incorporated in and constitute a part of this invention, illustrate one of the embodiments of the invention, and together with the description, serve to explain the principles of the invention in general terms. Like numerals refer to like parts throughout the disclosure.

BRIEF DESCRIPTION OF THE DRAWINGS

The foregoing aspects and other features of the present invention are explained in the following description, taken in connection with the accompanying drawings, wherein:

FIG. 3 is a detail longitudinal cross sectional view of a lead system utilizing the stylet unit of the invention;

FIG. 3A is a detail longitudinal cross sectional view, similar to FIG. 3, of a lead system utilizing a conventional stylet;

FIG. 4 is a plan view of a stylet unit embodying the invention;

FIG. 4A is an enlarged plan view of one embodiment of a novel stylet unit according to the invention;

FIG. 4B is an enlarged plan view of another embodiment of a novel stylet unit according to the invention;

FIG. 4C is an enlarged plan view of still another embodiment of a novel stylet unit according to the invention;

FIG. 4D is an enlarged plan view of a further embodiment of a novel stylet unit according to the invention.

FIG. 5 is a detail cross sectional view of the distal end of a lead system employing a guidewire for the implanting operation; and FIG. 6 is a detail cross sectional view of the distal end of the lead system of FIG. 5 instead employing a stylet embodying the invention for the implanting operation.

DETAILED DESCRIPTION OF THE PREFERRED EMBODIMENT

Figure 1:
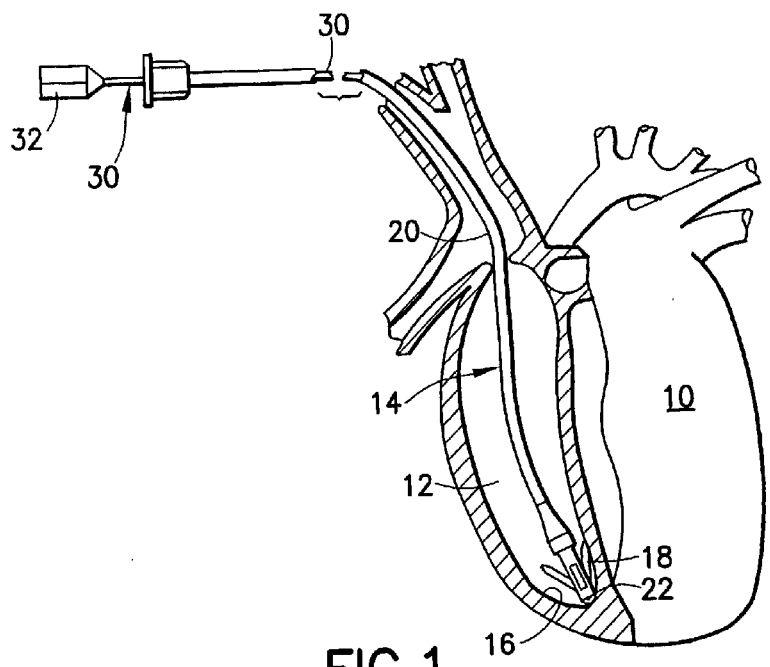
FIG. 1 is an elevation view illustrating a heart with a portion cut away to reveal an implantable lead system secured therein to a wall of the heart and with which the invention is employed.
Figure 2:
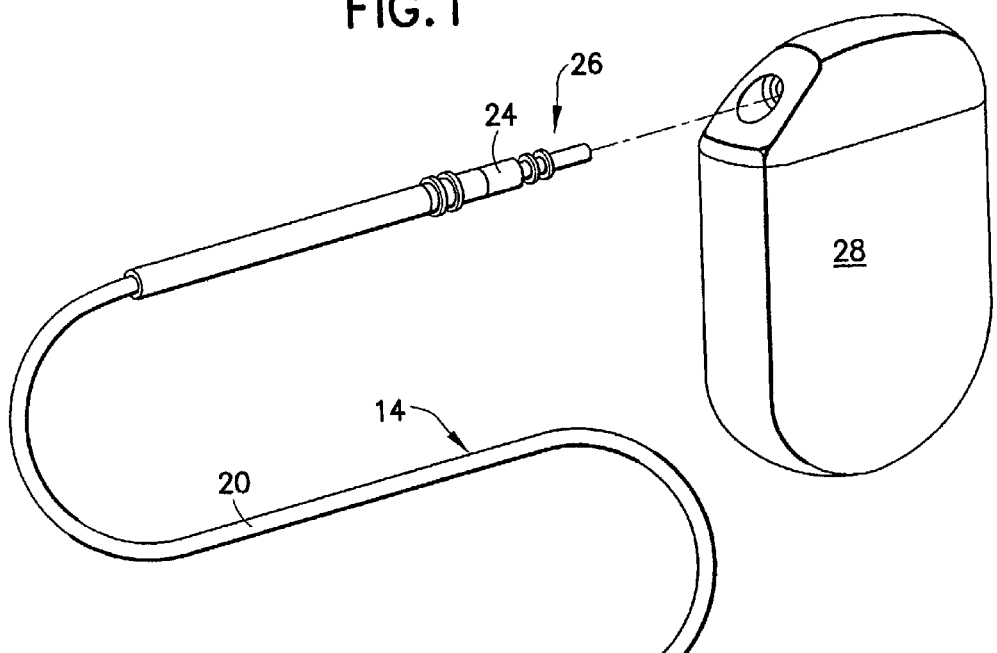
FIG. 2 is a perspective view of a typical implantable lead with which the invention is employed in combination with a stimulating device such as a pacemaker.

Referring to FIG. 1, there is shown a diagrammatic elevation view partially cut away and shown in section of a heart 10 into the right ventricle 12 of which is inserted a body implantable lead system 14 of the endocardial type incorporating features of the present invention. Although the present invention will be described with reference to the embodiments shown in the drawings, it should be understood that the present invention may be embodied in many alternate forms or embodiments. For example, while the illustrated lead system is of the passive fixation variety, it is within the scope of this invention that it be of the active fixation variety. In addition, any suitable size, shape or type of elements or materials consistent with the invention could be used. In this instance, the lead system 14 is attached to an interior wall 16 of the heart 10 by means of fixing tines 18 which engage the tissue or trabeculae of the heart.

As further illustrated, the lead system 14 also includes an insulating sheath 20 interconnecting a distal electrode 22 secured adjacent the interior wall 16 and a proximal electrical connector 24 at a proximal end 26 to which can be attached a source of electrical energy such as a pacemaker 28 (FIG; 2). In FIG. 1, a stylet unit 30 is illustrated inserted within the insulating sheath 20 and may be used to provide rigidity to the lead system 14 during insertion of the lead into the heart 10. A finger grip 32 is suitably provided at a proximal extremity of the stylet unit 30 for its manipulation.

In a more detailed setting, viewing FIG. 3, the lead system 14 includes a coil conductor 34 which is coupled to the distal electrode 22 and to the proximal electrical connector 24 in a customary fashion and is surrounded by the insulating sheath 20 which defines an axially extending lumen 35 extending between a proximal end 36 and a distal end 38.

Turning now to FIGS. 4, 4A, 4B, 4C, and 4D, the stylet unit 30 for implanting the lead system 14 includes an elongated main body 40 extending between proximal and distal ends, 42, 44, respectively. As will be seen below, the main body 40 has a width greater at the proximal end than at the distal end.

More specifically, in the embodiment illustrated in FIG. 4A, a main body 40A of a stylet unit 30A includes a proximal region 42 of substantially constant width, a distal region 44 of substantially constant width smaller than that of the proximal region, and an integral transition zone 46 interconnecting the proximal region and the distal region.

In the embodiment illustrated in FIG. 4B, a main body 40B of a stylet unit 30B is tapered between a proximal end 48 and a distal end 50.

Turning back to FIG. 4A, the stylet unit 30A is formed with an enlarged distal feature 52 at the extremity of the distal end 44. The enlarged distal feature 52 is coaxial with the main body, has a substantially uniform width, has a rounded blunt tip end 54 which may be hemispherical, for example, a width 56 greater than the width of the distal end 44 of the main body 40A, and a length 58 greater than the width 56. In another manner of description, it can be said that the enlarged distal feature 52 has opposed sides substantially parallel with the axis of the main body and semicircular proximal and distal ends 54, 59 which are tangential, respectively, with the opposed sides. An aft end 59 may be similarly but oppositely contoured relative to the tip end 54 although it may be of any other suitable shape as well.

Returning now to FIG. 4B, the stylet unit 30B is similarly formed with an enlarged distal feature 60 at the extremity of the distal end 50. The enlarged distal feature 60 has a rounded blunt tip end 62, a width 64 greater than the width of the distal end 50 of the main body 30B, and a length 66 greater than the width 64. In actual fact, the enlarged distal feature 60 is generally similar to the enlarged distal feature 52 except that its length 66 is substantially longer than the length 58 of the enlarged distal feature 52. By way of example, the length 58 of the enlarged distal feature 52 may be three times the radius of curvature of the blunt tip end 54 while the length 66 may be six times the radius of curvature of the blunt tip end 62 but, in any event more than three times the radius of curvature of the blunt tip end 62. The teaching of the invention, however, does not have to do with specific dimensions but only requires that all enlarged distal features have a length which is greater than the width.

Turning back to FIG. 3, it was earlier explained that the lead system 14 includes an elongated coil conductor 34 with a plurality of coil windings surrounded by the insulating sheath 20 defining a lumen 35 for receiving the coil conductor. Inner surfaces 68 of the coil conductor 34 face toward the center of a passageway 70 defined by the coil conductor and, in this instance, the stylet unit 30B is illustrated as being received in the passageway 70 with its enlarged distal feature 60 at its extreme distal end. It is seen by carefully examining FIG. 3 that the enlarged distal feature 60 is sufficiently long that it is able to advance in the direction of an arrow 72 along the passageway 70 in slidable engagement with the inner surfaces 68 of the coil conductor 34 without thrusting between adjoining coils 74, 76. Of course, it will be appreciated that the enlarged distal feature 52 of the stylet unit 30A would also successfully advance in slidable engagement with the inner surfaces 68 of the coil conductor 34 without thrusting between adjoining coils 74, 76. Indeed, any enlarged distal feature which is non spherical, whose diameter is generally equal to or slightly less than the diameter of the passageway 70 and whose length is greater than its width or diameter would serve the purposes of the invention and would not thrust between the adjoining coils 74, 76. This is in contrast to the construction of known stylets such as those presented in the earlier mentioned U.S. patents, namely, U.S. Pat. Nos. 5,807,339, 5,728,148, and 5,722,425. This undesirable situation occasioned by the prior art is illustrated in FIG. 3A which depicts a conventional stylet 78 received in the passageway 70 of the coil conductor 34. In this instance, a ball tip 80 at the extreme distal end of the stylet 78 is in the shape of a ball or sphere such that, as a curve in the lead system 14 is approached, the ball tip 80 thrusts between the adjoining coils 74, 76. As illustrated, the ball tip 80 is in engagement with the insulating sheath 20, causing a bulge 82 to occur in the sheath. With continued advancement of the conventional stylet 78, the ball tip 80 may actually pierce the insulating sheath 20 with undesirable consequences.

Other embodiments of the invention are illustrated in FIGS. 4C and 4D. In FIG. 4C, an enlarged distal feature 84 of a main body 40C of a modified stylet 30C is generally elliptical in shape having a major axis substantially coaxial with the main body. In FIG. 4D, and enlarged distal feature 86 is also illustrated which is generally elliptical in shape and has a major axis substantially coaxial with a main body 40D. In this instance, the enlarged distal feature 86 is substantially longer than the feature 84.

Leads that are used with guidewires to gain access to the coronary venous system must have an open lumen at the distal tip of the lead to allow the guidewire to pass through. In this regard, turn now to FIG. 5. Here, a lead system 88 is illustrated as including a coil conductor 90 coupled to a distal electrode 92, the conductor being surrounded by an insulating sheath 94. The distal electrode 92 has an aperture 96 for reception therethrough of a guidewire 98 for use in implanting the lead. However, when an implanting physician finds that the guidewire method is not successful, it is possible that the present invention can be successfully used. To this end, now viewing FIG. 6, the present invention is designed such that an enlarged distal tip end 100 of a stylet 101 will pass through a lumen 102 of the lead but stops at the distal electrode 92. More specifically, the distal electrode 92 is formed with a proximally facing bearing surface 104 for engageably receiving the distal tip end of the stylet. To assure this result, the distal tip end 100 has a width greater than that of the aperture 96 of the distal electrode 92 with the result that the stylet can selectively be used for implanting the lead system in place of the guidewire. This prevents the enlarged distal tip of the stylet from proceeding through the distal tip of the lead and causing undesirable consequences such as perforation of the vein into the pericardial sac, which in turn can cause tamponade.

This illustrates that the present invention is compatible with all designs of leads.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A removable implantable cardiac stimulation lead system for use with an implantable stimulation device, the lead system comprising:
   a lead comprising a proximal connector coupled to a distal electrode by a conductor, the conductor being surrounded by an insulating sheath and comprising an axially extending lumen therein; and
   a stylet unit for implanting the lead system and comprising:
      an elongated main body extending between proximal and distal ends and defining a width at the proximal end greater than at the distal end, wherein at least a portion of the main body is dimensioned for passage through the axially extending lumen; and
      an enlarged feature at the distal end of the main body comprising a rounded tip end, a width greater than the width of the distal end of the main body, and a length greater than the width;
   wherein the distal electrode has an aperture for reception therethrough of a guidewire for use in implanting the lead and a proximally facing bearing surface for engageably receiving the tip end of the stylet, the tip end defining a width greater than that of the aperture of the distal electrode; and
   wherein the stylet can selectively be used for implanting the lead system in place of the guidewire.

2. A lead system as set forth in claim 1:
   wherein the main body of the stylet is tapered between the proximal end and the distal end.

3. A lead system as set forth in claim 1:
   wherein the main body of the stylet comprises a proximal region of substantially constant width, a distal region of substantially constant width smaller than that of the proximal region, and an integral transition zone interconnecting the proximal region and the distal region.

4. A lead system as set forth in claim 1:
   wherein the enlarged distal feature of the stylet is coaxial with the main body and has a substantially uniform width.

5. A lead system as set forth in claim 4:
wherein the enlarged distal feature of the stylet has opposed sides substantially parallel with the axis of the main body and semicircular proximal and distal ends which are tangential, respectively, with the opposed sides thereof.

6. A lead system as set forth in claim 1:
wherein the enlarged distal feature is generally elliptical in shape and defines a major axis substantially coaxial with the main body.

7. A lead system as set forth in claim 1 comprising:
a finger grip at a proximal extremity of the elongated main body for manipulating the stylet unit.

8. A lead system as set forth in claim 1:
wherein an elongated tubular lead body contains an elongated coil conductor with a plurality of coil windings defining a passageway extending the length of the coil conductor and defining inner surfaces facing toward the passageway, the enlarged feature being sufficiently long to advance along the passageway in slidable engagement with the inner surfaces of the coil conductor but without thrusting between adjoining coils.

* * * * *